US012781221B2

(12) United States Patent
Tsuruya et al.

(10) Patent No.: US 12,781,221 B2
(45) Date of Patent: Nov. 3, 2026

(54) NUCLEIC ACID CONSTRUCT

(71) Applicant: Toray Industries, Inc., Tokyo (JP)

(72) Inventors: Atsuki Tsuruya, Kamakura (JP); Hiroyuki Kurihara, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 343 days.

(21) Appl. No.: 18/708,422

(22) PCT Filed: Nov. 15, 2022

(86) PCT No.: PCT/JP2022/042317
§ 371 (c)(1),
(2) Date: May 8, 2024

(87) PCT Pub. No.: WO2023/090305
PCT Pub. Date: May 25, 2023

(65) Prior Publication Data

US 2025/0304954 A1 Oct. 2, 2025

(30) Foreign Application Priority Data

Nov. 16, 2021 (JP) ................................ 2021-186193

(51) Int. Cl.
*C12N 15/11* (2006.01)
*C12N 1/02* (2006.01)
*C12N 1/165* (2026.01)
*C12R 1/645* (2006.01)

(52) U.S. Cl.
CPC ................ *C12N 15/11* (2013.01); *C12N 1/02* (2013.01); *C12N 1/165* (2021.05); *C12R 2001/645* (2021.05)

(58) Field of Classification Search
None
See application file for complete search history.

(56) References Cited

U.S. PATENT DOCUMENTS

2009/0269812 A1 10/2009 Sawai et al.
2011/0177551 A1 7/2011 Mimitsuka et al.
2015/0240250 A1 8/2015 Kobayashi et al.
2019/0153453 A1 5/2019 Hara et al.

FOREIGN PATENT DOCUMENTS

JP 2010-227031 10/2010
WO 2007/097260 8/2007
WO 2010/038613 4/2010
WO 2014/030644 2/2014
WO 2015/076393 5/2015

OTHER PUBLICATIONS

Holger Andree, et al. Expression of the human TPT1 gene coding for translationally controlled tumor protein (TCTP) is regulated by CREB transcription factors, Gene, vol. 380, Issue 2, 2006, pp. 95-103, ISSN 0378-1119, (Year: 2006).*
Chen W, Wang H, Tao S, Zheng Y, Wu W, Lian F, Jaramillo M, Fang D, Zhang DD. Tumor protein translationally controlled 1 is a p53 target gene that promotes cell survival. Cell Cycle. Jul. 15, 2013;12(14):2321-8. (Year: 2013).*
International Search Report dated Jan. 31, 2023, of counterpart International Application No. PCT/JP2022/042317, along with an English translation.
Giga-Hama Y et al., "High-Level Expression of Human Lipocortin I in the Fission Yeast *Schizosaccharomyces pombe* Using a Novel Expression Vector," *Bio/Technology*, 12: pp. 400-404, May 1994. http://www.nature.com/naturebiotechnology.
Suyama A et al., "Production of 3-hydroxypropionic acid via the malonyl-CoA pathway using recombinant fission yeast strains," *Journal of Bioscience and Bioengineering*, 124(4): pp. 392-399, Oct. 2017.
Karlin, S. and Altschul, F., "Applications and statistics for multiple high-scoring segments in molecular sequences," *Proc. Natl. Acad. Sci.*, 90(12): pp. 5873-7, Jun. 15, 1993. https://pubmed.ncbi.nlm.nih.gov/8390686/.
USC Dornsife, "Working With Pombe: Vectors," *PombeNet Forsburg Lab*, May 6, 2024, https://dornsife.usc.edu/pombenet/vectors/.
Suga, M., and Hatakeyama, T., "A rapid and simple procedure for high-efficiency lithium acetate transformation of cryopreserved *Schizosaccharomyces pombe* cells," *Yeast*, 22(10): pp. 799-804, Jul. 30, 2005. Abstract Only. https://pubmed.ncbi.nlm.nih.gov/16088874/.
Aoki, K. and Hironori, N., "Transformation of *Schizosaccharomyces japonicus*," *Cold Spring Harb Protoc*, pp. 996: 998, Jul. 21, 2017.
Amelina, H. et al., "Sequential and counter-selectable cassettes for fission yeast," *BMC Biotechnology*, 16(76): pp. 1-15, Nov. 8, 2016. https://link.springer.com/article/10.1186/s12896-016-0307-4.
Angad, G., "A lncRNA-regulated gene expression system with rapid induction kinetics in the fission yeast *Schizosaccharomyces pombe,*" *Cold Spring Harbor Laboratory Press for the RNA Society*, 26(11): pp. 1743-1752, 2020. https://rnajournal.cshlp.org/content/26/11/1743.full.pdf+html.
Matsuyama, M. et al., "pDUAL, a multipurpose, multicopy vector capable of chromosomal integration in fission yeast," Yeast Nov. 21(15): 1289-305, Nov. 2004, Abstract Only. https://pubmed.ncbi.nlm.nih.gov/15546162/.
Schmitt, M. E. et al., "A rapid and simple method for preparation of RNA from *Saccharomyces cerevisiae*," Nucleic Acids Research, 18(10): 3091-3092, Mar. 30, 1990.

* cited by examiner

*Primary Examiner* — Tracy Vivlemore
*Assistant Examiner* — Adam Michael Smith
(74) *Attorney, Agent, or Firm* — DLA Piper LLP

(57) ABSTRACT

The continuous culture of a *Schizosaccharomyces* yeast containing a nucleic acid construct which contains a translationally controlled tumor protein (TCTP) gene promoter derived from a *Schizosaccharomyces* yeast, and a polynucleotide fragment, and in which the polynucleotide fragment is artificially linked to the downstream of the promoter to be expressed under the control of the promoter, allows the polynucleotide fragment under the control of the promoter to be highly expressed.

12 Claims, 1 Drawing Sheet

Specification includes a Sequence Listing.

NUCLEIC ACID CONSTRUCT

CROSS REFERENCE TO RELATED APPLICATIONS

This application is a US national stage filing under 35 U.S.C. § 371 of International Application No. PCT/JP2022/042317, filed Nov. 15, 2022, which claims priority to Japanese Patent Application No. 2021-186193 filed Nov. 16, 2021, each of which is incorporated herein by reference in its entirety.

REFERENCE TO AN ELECTRONIC SEQUENCE LISTING

The contents of the electronic sequence listing (TOR-24-1075_SL.xml; Size: 11,304 bytes; and Date of Creation: Nov. 12, 2024) is herein incorporated by reference in its entirety.

TECHNICAL FIELD

This disclosure relates to a nucleic acid construct capable of expressing a polynucleotide in a *Schizosaccharomyces* yeast.

BACKGROUND

*Schizosaccharomyces* yeasts are one type of microbial model organisms, and their applications in the production of proteins and chemical products have been studied. To produce a protein or a chemical product using a microorganism, it is necessary to express a polynucleotide encoding an enzyme gene in the microorganism, and a promoter is required to achieve this end.

A promoter is a nucleic acid sequence that controls the expression of a polynucleotide linked downstream of the promoter, and examples of the type of the promoter include those that allow for constitutive expression, and those that allow for inducible expression. CMV promoter (Giga-Hama Y et al., Bio/Technology, 12, 400-404 (1994)), hsp9 promoter, nmt1 promoter (Suyama A et al., J. Biosci. Bioeng, Vol. 124, 4, 392-399 (2017)) and the like are known as the promoters which can be used in *Schizosaccharomyces* yeasts.

In the method of producing a protein or a chemical product by culturing a microorganism, batch fermentation, fed-batch fermentation or continuous culture is used as the culture method. Of these, continuous culture has characteristics that it is less susceptible to substrate inhibition or product inhibition, and that the productivity increases. Therefore, in the method of producing an enzyme or a chemical product using a genetically engineered microorganism, an increase in the production efficiency of the protein or the chemical is expected, by: preparing a nucleic acid construct in which a polynucleotide, which is a recombinant gene, is linked to the downstream of a promoter which is highly expressed in continuous culture; and continuously culturing a genetically engineered microorganism into which the thus prepared nucleic acid construct is introduced. However, there is a newly discovered problem that a nucleic acid construct using a known promoter does not function sufficiently, in the continuous culture of a recombinant *Schizosaccharomyces* yeast.

It could therefore be helpful to provide a nucleic acid construct containing a promoter which is highly expressed in the continuous culture of a *Schizosaccharomyces* yeast, a *Schizosaccharomyces* yeast into which the construct is introduced, and a method of expressing a polynucleotide of interest included in the construct.

SUMMARY

We comprehensively analyzed the gene expression of *Schizosaccharomyces* yeasts, and studied intensively to solve the above-mentioned problem. As a result, we have found out that the above-mentioned problem can be solved by a nucleic acid construct containing a translationally controlled tumor protein (TCTP) gene promoter derived from a *Schizosaccharomyces* yeast.

We Thus Provide (1) to (12):

(1) A nucleic acid construct, containing a translationally controlled tumor protein (TCTP) gene promoter derived from a *Schizosaccharomyces* yeast, and a polynucleotide fragment, wherein the polynucleotide fragment is artificially linked to the downstream of the promoter to be expressed under the control of the promoter.

(2) The nucleic acid construct according to (1), wherein the *Schizosaccharomyces* yeast is *Schizosaccharomyces pombe, Schizosaccharomyces octosporus, Schizosaccharomyces cryophilus* or *Schizosaccharomyces japonicus.*

(3) The nucleic acid construct according to (1) or (2), wherein the promoter contains the 5'-untranslated region of the TCTP gene, and the polynucleotide fragment is artificially linked to the downstream of the untranslated region.

(4) The nucleic acid construct according to any one of (1) to (3), wherein the promoter is a polynucleotide containing the nucleotide sequence of (a) or (b):

(a) a polynucleotide composed of the nucleotide sequence of any one of SEQ ID NOs: 1 to 4;

(b) a polynucleotide composed of a nucleotide sequence having a sequence identity of 85% or more to the nucleotide sequence of any one of SEQ ID NOs: 1 to 4.

(5) The nucleic acid construct according to any one of (1) to (3), wherein the promoter is a polynucleotide containing the nucleotide sequence of (c) or (d):

(c) a polynucleotide composed of the nucleotide sequence of any one of SEQ ID NOs: 5 to 8;

(d) a polynucleotide composed of a nucleotide sequence having a sequence identity of 85% or more to the nucleotide sequence of any one of SEQ ID NOs: 5 to 8.

(6) The nucleic acid construct according to any one of (1) to (5), wherein the polynucleotide fragment encodes a protein.

(7) A recombinant *Schizosaccharomyces* yeast, containing the nucleic acid construct according to any one of (1) to (6).

(8) A method of expressing a polynucleotide, the method including the step of continuously culturing the recombinant *Schizosaccharomyces* yeast according to (7).

(9) The method of expressing a polynucleotide according to (8), wherein the continuous culture includes the step of filtering a culture liquid obtained by culturing the yeast through a separation membrane, retaining or returning the unfiltered liquid containing the yeast in or to the culture liquid, and adding a fermentation feedstock to the culture liquid.

(10) A method of producing a chemical product, the method including the step of culturing the recombinant *Schizosaccharomyces* yeast according to (7).

(11) The method of producing a chemical product according to (10), wherein the culture is continuous culture.

(12) The method of producing a chemical product according to (11), wherein the continuous culture includes the step of filtering a culture liquid obtained by culturing the yeast through a separation membrane, retaining or returning the unfiltered liquid containing the yeast in or to the culture liquid, and adding a fermentation feedstock to the culture liquid.

The use of the nucleic acid construct allows the polynucleotide fragment linked to the promoter to be highly expressed in a *Schizosaccharomyces* yeast, during the continuous culture thereof. Therefore, our construct is useful in the production of a protein or a chemical product using a *Schizosaccharomyces* yeast.

BRIEF DESCRIPTION OF THE DRAWING

The FIGURE shows the results of the multiple alignment of nucleotide sequences (SEQ ID NOs: 5 to 8) having TCTP promoter activity.

DETAILED DESCRIPTION

Figure 1:
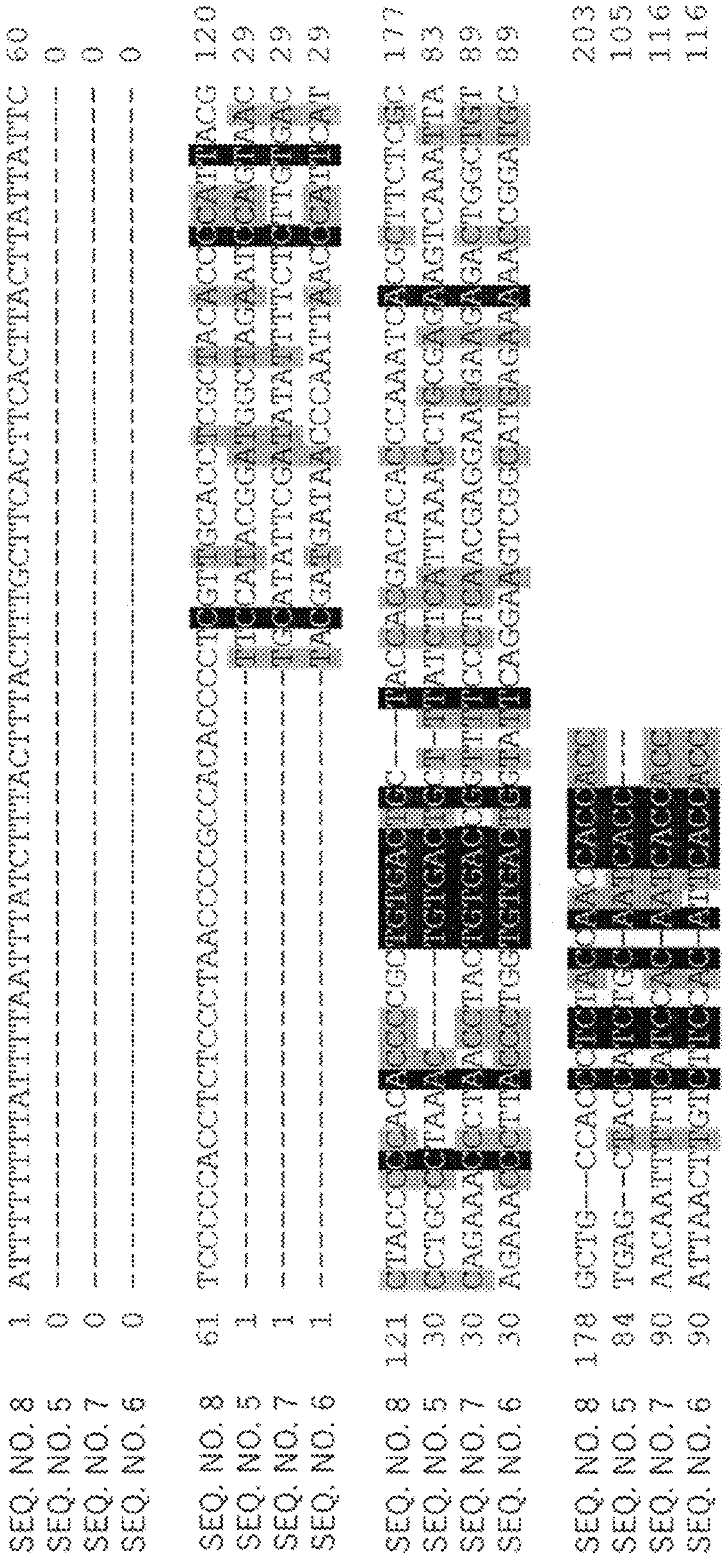

The scientific and technical terms used in relation with this disclosure have meanings generally understood by those skilled in the art, unless otherwise defined.

The term "*Schizosaccharomyces* yeast" refers to a yeast that taxonomically belongs to the genus *Schizosaccharomyces*. Examples of such a yeast include: *Schizosaccharomyces cryophilus, Schizosaccharomyces japonicus, Schizosaccharomyces kambucha, Schizosaccharomyces octosporus, Schizosaccharomyces osmophilus, Schizosaccharomyces versatilis, Schizosaccharomyces malidevorans* and *Schizosaccharomyces pombe.*

The "sequence identity" between nucleotide sequences refers to the degree of matching between two or more nucleotide sequences that can be compared with one another. That is, the higher the identity between two certain nucleotide sequences, the higher the identity or similarity between these sequences. The degree of identity between nucleotide sequences is determined, for example, using FASTA, which is a tool for sequence analysis, with default parameters. Alternatively, the degree of identity can be determined using BLAST (Proc. Natl. Acad. Sci. 90:5873-7 (1993)), which is an algorithm by Karlin and Altschul. Specific techniques to perform these analysis methods are well known, and the web site (http://www.ncbi.nlm.nih.gov/) of the National Center of Biotechnology Information (NCBI) can be referred to.

1. Nucleic Acid Construct

Our nucleic acid construct contains a translationally controlled tumor protein (TCTP) gene promoter derived from a *Schizosaccharomyces* yeast, and a polynucleotide fragment, and the polynucleotide fragment is artificially linked to the downstream of the promoter so that the polynucleotide fragment is expressed under the control of the promoter.

The translationally controlled tumor protein (TCTP) gene promoter derived from a *Schizosaccharomyces* yeast (hereinafter, also simply referred to as "TCTP promoter") is not particularly limited, as long as the promoter is a DNA sequence that controls the expression of the TCTP gene in the wild type of the microorganism.

Examples of the TCTP gene of a *Schizosaccharomyces* yeast include *Schizosaccharomyces pombe* TCTP gene (NCBI Accession Number: NM_001019749), *Schizosaccharomyces octosporus* TCTP gene (NCBI Accession Number: XM_013161615), *Schizosaccharomyces cryophilus* (NCBI Accession Number: XM_013168673.1) and *Schizosaccharomyces japonicus* (NCBI Accession Number: XM_002173941.2). The TCTP promoter derived from any of these yeasts is preferably used.

The nucleotide sequence of a promoter of a gene includes the upstream (5'-side) and, if necessary, the downstream (3'-side), of the transcription start site, as is obvious to those skilled in the art. The method of identifying the transcription start site is not particularly limited, and the transcription start site can be identified by the sequence information of the mRNA or by various types of databases. For example, the transcription start site of the TCTP gene of *Schizosaccharomyces pombe* can be identified by the mRNA sequence of the TCTP gene which can be obtained from the NCBI Reference Sequence: NM_001019749.2.

When the nucleotide at the transcription start of the TCTP gene of a *Schizosaccharomyces* yeast is defined as +1, a nucleotide downstream (3'-side) thereof is defined as a positive (+) value, and a nucleotide upstream (5'-side) thereof is defined as 0 or a negative (−) value, the TCTP promoter may preferably be, for example, any nucleic acid region including the transcription start site, extending from −1,000 to +200, more preferably from −500 to +150, and still more preferably from −150 to +150. Specific examples thereof include the nucleotide sequences of SEQ ID NOs: 1 to 8. The nucleotide sequence of any one of SEQ ID NOs: 5 to 8 is preferred, and the nucleotide sequence of SEQ ID NO: 5 is more preferred.

The nucleotide sequences of SEQ ID NOs: 1 to 4 are, the nucleic acid region from −359 to +41 of the TCTP gene on the genome of *Schizosaccharomyces pombe*, the nucleic acid region from −194 to +22 of the TCTP gene on the genome of *Schizosaccharomyces octosporus*, the nucleic acid region from −333 to +8 of the TCTP gene on the genome of *Schizosaccharomyces cryophilus*, and the nucleic acid region from −242 to +133 of the TCTP gene on the genome of *Schizosaccharomyces japonicus*, respectively.

The nucleotide sequences of SEQ ID NOs: 5 to 8 are, the nucleic acid region from −64 to +41 of the TCTP gene on the genome of *Schizosaccharomyces pombe*, the nucleic acid region from −94 to +22 of the TCTP gene on the genome of *Schizosaccharomyces octosporus*, the nucleic acid region from −108 to +8 of the TCTP gene on the genome of *Schizosaccharomyces cryophilus*, and the nucleic acid region from −70 to +133 of the TCTP gene on the genome of *Schizosaccharomyces japonicus*, respectively. The FIGURE shows the results of the multiple alignment of the nucleotide sequences of SEQ ID NOs: 5 to 8, aligned by Clustal W2 (setting: default).

The TCTP promoter may have a mutation in the nucleotide sequence, as long as the promoter has the promoter activity. Examples of the mutation in the nucleotide sequence include substitution, deletion, insertion and addition. In this example, the nucleotide sequence of the promoter having a mutation preferably has an identity of 85% or more, more preferably 90%, and still more preferably 95% or more, to the nucleotide sequence of any one of SEQ ID NOs: 1 to 8.

In the nucleic acid construct, the polynucleotide fragment is linked to be expressed under the control of the TCTP promoter. The expression "to be expressed under the control of the promoter" refers to the fact that one or more of the level of expression, the time of expression, the manner of expression, the site of expression and the like, of the linked polynucleotide fragment are controlled by a specific promoter, and is not limited to the control by the specific promoter alone. That is, the expression level and/or the like of the polynucleotide fragment may change due to a factor(s) other than the TCTP promoter. For example, the method of controlling the expression may be added by adding a new activator and/or the like.

The polynucleotide fragment is not particularly limited, as long as it is for allowing the fragment to be expressed under the control of the TCTP promoter, and may be a DNA sequence of any two or more nucleotides to the extent that this purpose is achieved. Further, the polynucleotide fragment may be a nucleotide sequence that encodes a protein, or may be a nucleotide sequence that expresses a functional nucleic acid that functions without encoding a protein, such as a precursor of a double-stranded RNA that triggers RNAi, or a ribozyme.

The method of artificially linking a polynucleotide fragment to be expressed under the control of the TCTP promoter is not particularly limited, and is obvious to those skilled in the art. The state of being "artificially linked" as used above refers to a state in which a polynucleotide fragment other than a wild type TCTP gene is linked to the downstream of the TCTP promoter.

The nucleic acid construct is not limited to a DNA sequence in which the TCTP promoter and a polynucleotide fragment alone are present, and may include another nucleotide sequence. For example, the nucleic acid construct may be one in which a terminator sequence for terminating the transcription of the polypeptide fragment is added to the 3'-end of the nucleic acid construct, one in which a restriction enzyme sequence is added to the 5'-end or the 3'-end of the nucleic acid construct, or one in which a restriction enzyme sequence is inserted into the nucleic acid construct, or may further be one in which the nucleic acid construct is incorporated into a plasmid.

The terminator sequence which can be added to the nucleic acid construct is not particularly limited, and examples thereof include adh1 terminator, sv40 terminator, tef terminator, nmt1 terminator and ura4 terminator.

The plasmid into which the nucleic acid construct is to be incorporated is not particularly limited, and it is possible to use plasmids shown in PombeNet (https://dornsife.usc.edu/pombenet/vectors/). Specific examples thereof include pAUR224 (available from Takara Bio Inc.), REP series, pKS series and pFA6a series.

The method to obtain the nucleic acid construct is not particularly limited, and the construct can be obtained by an ordinary chemical synthesis method or genetic engineering technique. For example, the nucleic acid construct can be obtained by artificially synthesizing a DNA in which a polynucleotide fragment is linked to the downstream of the TCTP promoter, based on the information of the nucleotide sequences registered to NCBI and the like. A service provided by GENEWIZ Inc. or the like, for example, can be used for the artificial synthesis of the DNA. Alternatively, the construct can be obtained by cloning the promoter sequence from a microorganism such as *Schizosaccharomyces pombe*, in accordance with the method described, for example, in "Molecular Cloning-A LABORATORY MANUAL THIRD EDITION (Joseph Sambrook, David W. Russell, Cold Spring Harbor Laboratory Press, 2001)", and linking a polynucleotide fragment of interest, for example, by the restriction enzyme method or the homologous recombination method. The homologous recombination method can be performed, for example, by using "In Fusion" available from Takara Bio Inc., or the like.

2. Recombinant *Schizosaccharomyces* Yeast

A recombinant *Schizosaccharomyces* yeast including the above-described nucleic acid construct, and a method of expressing a polynucleotide located downstream of the TCTP promoter included in the nucleic acid construct, using the recombinant yeast, are provided each as one embodiment.

The method of introducing the nucleic acid construct into a *Schizosaccharomyces* yeast is not particularly limited. The method may be, for example, the lithium acetate method or the electroporation method, which is commonly used in yeast recombination. In *Schizosaccharomyces pombe*, it is possible to efficiently obtain a transformant by the method described in "Yeast, 22:799-804 (2005)". In *Schizosaccharomyces japonicus*, the transformation method thereof is described in "Cold Spring Harb. Protoc., 996:998 (2017)".

As one embodiment of introducing the nucleic acid construct into a *Schizosaccharomyces* yeast, there is a method of introducing the nucleic acid construct onto the genome of the *Schizosaccharomyces* yeast. The nucleic acid construct can be introduced onto the genome, by a method in which a DNA fragment obtained by linking a DNA fragment having a nucleotide sequence homologous to that of the locus of a genomic DNA intended to be introduced, a selectable marker cassette and the nucleic acid construct is introduced into the yeast. At this time, it is also possible to use a genome editing technology such as the Cre/LoxP system or CRISPR-Cas9. The introduction of a DNA of interest onto the genomic DNA of *Schizosaccharomyces pombe* can be performed by the method described in BMC Biotechnol., 16:76 (2016).

As one embodiment of introducing the nucleic acid construct into a *Schizosaccharomyces* yeast, there is a method of introducing a vector including the nucleic acid construct into the *Schizosaccharomyces* yeast. The method of obtaining a vector including the nucleic acid construct is not particularly limited, and is obvious to those skilled in the art. For example, the vector can be obtained by artificial synthesis, in the same manner as that of the nucleic acid construct described above. Alternatively, the construct can be linked to a vector that functions in a *Schizosaccharomyces* yeast by the restriction enzyme method or the homologous recombination method.

The vector that functions in a *Schizosaccharomyces* yeast is not particularly limited, as long as the vector can be stably maintained in a host cell, and replicated in a microorganism. Examples of the vector include pAUR224 (available from Takara Bio Inc.), pTIN (RNA, 26 (11): 1743-1752 (2020)) and pDUAL series (Yeast, November; 21 (15): 1289-305 (2004)).

3. Method of Expressing Polynucleotide

The TCTP promoter included in the nucleic acid construct suitably functions in the continuous culture of a *Schizosaccharomyces* yeast, and thus, the polynucleotide fragment linked downstream of the TCTP promoter can be suitably expressed in a recombinant yeast into which the nucleic acid construct has been introduced, by continuously culturing the recombinant yeast. The "continuous culture" refers to a culture method in which the supply of a fed-batch liquid and the withdrawal of the culture liquid are performed from an appropriate time point. The time point of addition, the composition, the rate of addition and the method of addition, and the like, of the fed-batch liquid are not particularly limited. The time point for starting the supply of the fed-batch liquid need not necessarily be the same as the time point for starting the withdrawal of the culture liquid. Further, the supply of the fed-batch liquid and the withdrawal of the culture liquid may be performed continuously or intermittently. The continuous culture may be, for example, a continuous culture method using a chemostat or a separation membrane. Preferred is a continuous culture using a separation membrane.

The continuous culture using a separation membrane is a culture method which allows to maintain the yield or the productivity of a product at a high level for a long period of time, in culturing a microorganism to produce a chemical product, by: culturing the microorganism; filtering the culture liquid containing the microorganism through a separation membrane; collecting the product from the filtrate while retaining the filtered microorganism in the culture liquid at the same time, to maintain a high concentration of the microorganism in the culture liquid.

In the continuous culture using a separation membrane, once the supply of a fermentation feedstock and the filtration of the culture liquid is started, the supplied fermentation feedstock is metabolized by the microorganism. After a while, a steady state in which the microorganism grows at a constant rate is reached. Whether or not the steady state is reached can be determined by: analyzing the product contained in the filtrate, the concentration of the fermentation feedstock and the like; and confirming the fact that the production rate of the product, the concentration of unused fermentation feedstock and the like have reached constant.

The timing to collect the unfiltered liquid containing the recombinant yeast to be cultured is not limited as long as it is within the time period during which the continuous culture is being performed, namely, can be any time point after the start of the supply of the fermentation feedstock and the filtration of the culture liquid. However, it is preferred to collect the unfiltered liquid in the steady state. For example, it is preferred to collect the unfiltered liquid in the continuous culture in which the saccharide concentration in the filtrate is maintained preferably at 5 g/L or less, more preferably at 2 g/L or less, and still more preferably at 0.3 g/L or less, as the steady state, under the condition where the concentration of saccharides contained in the fermentation feedstock to be supplied is from 100 to 200 g/L. The "saccharide concentration" refers to the value of the total concentration of saccharides, as carbon sources that can be utilized by the yeast to be used in the culture. For example, when glucose and fructose are contained as carbon sources, the saccharide concentration refers the value of the total concentration thereof. When a polysaccharide such as sucrose is contained, the saccharide concentration is calculated in terms of the weight of monosaccharides that have been degraded from the polysaccharide.

The continuous culture using a separation membrane can be performed in accordance with a method known to those skilled in the art, for example, in accordance with the continuous culture method disclosed in WO 2007/097260 or WO 2010/038613.

EXAMPLES

Our construct will now be described specifically, with reference to Examples.

Reference Example 1 Analysis of Saccharides

The saccharide concentration was quantified by comparison with authentic samples under the HPLC conditions shown below.

Column: "Shodex SH1011" (manufactured by Showa Denko K.K.)
Mobile phase: 5 mm sulfuric acid (flow velocity: 0.6 mL/min)
Reaction liquid: none
Detection method: RI (differential refractive index)
Temperature: 65° C.

Reference Example 2 Continuous Culture Using Separation Membrane

Using *Schizosaccharomyces pombe* 972h- as the yeast, the culture of the yeast was carried out by a continuous culture using a separation membrane. Cane molasses purchased from Kasetphol Co., Ltd. was diluted with water to adjust the saccharide concentration, and the resulting solution was used as the fermentation feedstock. Specifically, a stock solution of the cane molasses and water were mixed, and a part of the mixture was aliquoted. The concentration of saccharides contained in the aliquot of the feedstock was analyzed by the method described in Reference Example 1. The specific gravity and the weight of the fermentation feedstock remaining after aliquoting were measured, to determine the volume. The total weight of the saccharides was calculated from the volume of the fermentation feedstock determined by the results of the saccharide analysis and the calculation. The saccharide concentration was adjusted by adding water thereto, the resultant was subjected to a sterilization treatment in an autoclave, and the sterilized solution was used as the fermentation feedstock in the following experiments. The analysis results of the saccharide concentration after preparing the fermentation feedstock are shown in Table 1.

The yeast was shake-cultured overnight in 10 mL of YPD culture medium (containing 100 g/L glucose (manufactured by Nacalai Tesque Inc.), 10 g/L dried yeast powder (manufactured by Nacalai Tesque Inc.) and 20 g/L "Bacto Peptone" (manufactured by Becton Dickinson Company, Ltd.)) (pre-preculture). The pre-preculture liquid was inoculated in 100 mL of fresh YPD culture medium, and shake-cultured in a 500 mL-baffle flask for 24 hours (preculture). The preculture liquid was introduced into a fermentation reaction vessel containing 15 mL of the fermentation feedstock described above, and the main culture was started. At the time point 24 hours after the start of the main culture, the continuous culture was started, and at the same time, the unfiltered culture liquid was collected for RNA extraction. The RNA sample obtained at this time was used as the batch phase in the expression analysis. After the start of the continuous culture, the saccharide concentration in the filtrate was analyzed by the method of Reference Example 1, the fact that glucose, fructose and sucrose were each maintained at 0 g/L was confirmed, and the unfiltered liquid for RNA extraction was collected. The RNA sample obtained at this time was used as the continuous culture phase in the expression analysis. Operation conditions for the continuous culture using a separation membrane are shown below.

Conditions for Continuous Culture Using Separation Membrane

Fermentation reaction vessel capacity: 2 L
Separation membrane used: filtration membrane made of polyvinylidene fluoride
Effective filtration area of membrane separation element: 218 $cm^2$
Temperature adjustment: 30° C.
Air flow rate in the fermentation reaction vessel: no air flow Stirring rate in the fermentation reaction vessel: 300 rpm Flux set value: 0.18 ($m^3/m^2$/day)

Flow velocity in cross-flow filtration: 100 (cm/sec)

Sterilization: The fermentation vessel including a separation membrane element was subjected to high pressure steam sterilization at 121° C. for 20 minutes in an autoclave.

Average pore diameter: 0.1 μm

Standard deviation of the average pore diameter: 0.035 μm

Membrane surface roughness: 0.06 μm

Pure water permeation coefficient: $50\times10^{-9}$ ($m^3/m^2$/sec/Pa)

Reference Example 3 Chemostat Culture

Using *Schizosaccharomyces pombe* 972h- as the yeast, the culture of the yeast was carried out by chemostat culture. Cane molasses purchased from Mitrphol Co., Ltd. was diluted with water to adjust the saccharide concentration, and the resulting solution was used as the fermentation feedstock. Specifically, a stock solution of the cane molasses and water were mixed, and a part of the mixture was aliquoted. The concentration of saccharides contained in the aliquot of the feedstock was analyzed by the method described in Reference Example 1. The specific gravity and the weight of the fermentation feedstock remaining after aliquoting were measured, to determine the volume. The total weight of the saccharides was calculated from the volume of the fermentation feedstock determined by the results of the saccharide analysis and the calculation. The saccharide concentration was adjusted by adding water thereto, the resultant was subjected to a sterilization treatment in an autoclave, and the sterilized solution was used as the fermentation feedstock in the following experiments. The analysis results of the saccharide concentration after preparing the fermentation feedstock are shown in Table 1.

The yeast was shake-cultured overnight in 10 mL of YPD culture medium (containing 100 g/L glucose (manufactured by Nacalai Tesque Inc.), 10 g/L dried yeast powder (manufactured by Nacalai Tesque Inc.) and 20 g/L "Bacto Peptone" (manufactured by Becton Dickinson Company, Ltd.)) (pre-preculture). The pre-preculture liquid was inoculated in 100 mL of fresh YPD culture medium, and shake-cultured in a 500 mL-baffle flask for 24 hours (preculture). The preculture liquid was introduced into a fermentation reaction vessel containing 15 mL of the fermentation feedstock described above, and the main culture was started. At the time point 24 hours after the start of the main culture, the continuous culture was started, and at the same time, the culture liquid for RNA extraction was collected. The RNA sample obtained at this time was used as the batch phase in the expression analysis. After the start of the continuous culture, the saccharide concentration in the fermentation liquid was analyzed by the method of Reference Example 1, the fact that glucose, fructose and sucrose were each maintained at 0 g/L was confirmed, and the culture liquid for RNA extraction was collected. The RNA sample obtained at this time was used as the continuous culture phase in the expression analysis. Operation conditions for the chemostat culture are shown below.

Chemostat Culture

Fermentation reaction vessel capacity: 2 L

Temperature adjustment: 30° C.

Air flow rate in the fermentation reaction vessel: no air flow

Stirring rate in the fermentation reaction vessel: 300 rpm

Sterilization: The fermentation vessel including a feedstock tank and a withdrawal line was subjected to high pressure steam sterilization at 121° C. for 20 minutes in an autoclave.

TABLE 1

| | | Concentration of Saccharides (g/L) | | | |
|---|---|---|---|---|---|
| | | Glucose | Fructose | Sucrose | Saccharide Concentration |
| Continuous Culture Using Separation Membrane (Reference Example 2) | Fermentation Feedstock 1 | 13.9 | 24.7 | 76.4 | 119.0 |
| | Fermentation Feedstock 2 | 13.9 | 24.2 | 76.4 | 118.5 |
| Chemostat Culture (Reference Example3) | Fermentation Feedstock 1 | 19.4 | 25.7 | 71.2 | 120.5 |
| | Fermentation Feedstock 2 | 18.2 | 25.4 | 72.0 | 119.4 |
| | Fermentation Feedstock 3 | 18.1 | 27.4 | 71.2 | 121.2 |

Example 1 Identification of Promoter (1) Total RNA Extraction

Five ml of the culture liquid collected for RNA extraction was aliquoted into a 15 m[1]-centrifugal tube, centrifuged (8,000×g, 5 minutes, 4° C.), and bacterial cells were collected. The collected bacterial cells were washed with sterile Milli-Q water. The RNA extraction was carried out based on the method described by Schmitt et al. (Nucl. Acids. Res., 18:3091-3092 (1990)). The collected RNA was finally dissolved in 20 to 50 μl of "UltraPure DNase/RNase-Free Distilled Water" (manufactured by Thermo Fisher Scientific, Inc.).

(2) Comprehensive Expression Level Analysis

A comprehensive expression level analysis was carried out using RNA-seq contract service (https://catalog.takara-bio.co.jp/jutaku/basic_info.php?unitid=U100006557sha-puanchor03) employing HiSeq System (Illumina, Inc.), provided by Takara Bio Inc. It is noted that the analysis method is as of 2017. The total RNA obtained in the section (1) was subjected to the comprehensive expression level analysis, to measure the expression levels of polynucleotides in the yeast. As a result, the expression level data of the polynucleotides were obtained as the sequence data of the respective polynucleotides, and as the annotation results and the FPKM (fragments per kilobase of exon per million reads mapped) values of the respective polynucleotides.

(3) Identification of Highly Expressed Promoter Sequence

Based on the expression level data and the annotation data obtained in the section (2), the expression levels of the respective polynucleotides in the batch fermentation phase and the continuous culture phase were compared, to identify a polynucleotide showing a high level of expression in the continuous culture. The upstream genomic DNA sequence was searched from the annotation information of the polynucleotide, to identify the promoter sequence.

As a result, it was found out that the TCTP gene is highly expressed in the continuous culture phase, and the sequence of SEQ ID NO: 1 was obtained as the promoter sequence. Table 2 shows the FPKM values of TCTP, and as references, the FPKM values of the genes (nmt1 and hsp9) of the promoters which are used in the study of the production of chemical products (J. Biosci. Bioeng., 124 (4): 392-399 (2017)), among known promoters.

TABLE 2

| | FPKM | |
|---|---|---|
| Name of Gene | Batch Phase | Continuous Culture Phase |
| Continuous Culture Using Separation Membrane | | |
| TCTP | 2870.4 | 6809.9 |
| nmt1 (Reference) | 9.2 | 11.3 |
| hsp9 (Reference) | 410.2 | 95.5 |
| Chemostat Culture | | |
| TCTP | 2319.8 | 3289.5 |
| nmt1 (Reference) | 3.9 | 9.6 |

Example 2 Preparation of Recombinant Yeast (1) Obtaining Plasmid Vector

A plasmid in which the TCTP promoter (hereinafter, also referred to as "TCTP1") of SEQ ID NO: 1 was introduced into the Nco1 and Xho1 sites, and the gene of a fluorescent protein, mRuby (FPbase ID: 6KLAW), was introduced into the Sac1 and Sal1 sites, of pAUR224 (available from Takara Bio Inc.), was designed, and pAURTCTP1-mRuby was obtained by the GENEWIZ gene synthesis service.

(2) Obtaining Transformant

The pAURTCTP1-mRuby obtained in the section (1) was introduced into *Schizosaccharomyces pombe* 972h-, by the method disclosed in Yeast, 22:799-804 (2005) with a partial modification. Specifically, bacterial cells after being heat-shocked by the method disclosed in the above-described paper were centrifuged at 8,000 rpm for 5 minutes, the supernatant was removed. Thereafter, 1 mL of YEL culture medium (containing 5 g/L dried yeast powder (manufactured by Nacalai Tesque Inc.) and 30 g/L glucose (manufactured by Nacalai Tesque Inc.)) was added to the cells, followed by allowing to stand at 30° C. for 6 hours. The bacterial cells after being left to stand was inoculated in YEA selective medium (YEL culture medium supplemented with 20 g/L purified agar powder (manufactured by Nacalai Tesque Inc.) and 0.5 μg/mL aureobasidin A (manufactured by Takara Bio Inc.)), and cultured at 30° C. for 4 days. The colonies formed were captured by a fluorescence image scanner ("PRINTGRAPH 2M" (manufactured by ATTO Corporation); LED: Cyan, exposure: 429 ms, filter: 595 nm), and fluorescent colonies were fished, to obtain a recombinant yeast pAURTCTP1-mRuby strain.

Example 3 Evaluation of Promoter Activity (1) Continuous Culture of Recombinant Yeast Using the recombinant yeast pAURTCTP1-mRuby strain, the culture of the yeast was carried out by continuous culture using a separation membrane. A 5-times concentrated YEL selective medium (containing 25 g/L dried yeast powder (manufactured by Nacalai Tesque Inc.), 90 g/L glucose (manufactured by Nacalai Tesque Inc.) and 0.5 μg/mL aureobasidin A (manufactured by Takara Bio Inc.)) was used as the fermentation feedstock. The recombinant yeast was shake-cultured overnight in 10 mL of YEL selective medium (containing 5 g/L dried yeast powder (manufactured by Nacalai Tesque Inc.), 30 g/L glucose (manufactured by Nacalai Tesque Inc.) and 0.5 μg/mL aureobasidin A (manufactured by Takara Bio Inc.)) (pre-preculture). The pre-preculture liquid was inoculated in 100 mL of fresh YEL selective medium, and shake-cultured in a 500 mL-baffle flask for 24 hours (preculture). The preculture liquid was introduced into a fermentation reaction vessel containing 15 mL of the fermentation feedstock described above, and the main culture was started. At the time point 24 hours after the start of the main culture, the continuous culture was started. At this time, the culture liquid for evaluating the activity was collected. After the start of the continuous culture, the saccharide concentration in the filtrate was analyzed by the method of Reference Example 1, the fact that glucose was maintained at 0 g/L was confirmed, and the unfiltered liquid for evaluating the activity was collected. Operation conditions for the continuous culture using a separation membrane are shown below.

Conditions for Continuous Culture Using Separation Membrane

- Fermentation reaction vessel capacity: 2 L
- Separation membrane used: filtration membrane made of polyvinylidene fluoride
- Effective filtration area of membrane separation element: 218 $cm^2$
- Temperature adjustment: 30° C.
- pH control during fermentation: 4.0
- Air flow rate in the fermentation reaction vessel: no air flow
- Stirring rate in the fermentation reaction vessel: 300 rpm
- Flux set value: 0.18 ($m^3/m^2$/day)
- Flow velocity in cross-flow filtration: 50 (cm/sec)
- Sterilization: The fermentation vessel including a separation membrane element was subjected to high pressure steam sterilization at 121° C. for 20 minutes in an autoclave.
- Average pore diameter: 0.1 μm
- Standard deviation of the average pore diameter: 0.035 μm
- Membrane surface roughness: 0.06 μm
- Pure water permeation coefficient: $50\times10^{-9}$ ($m^3/m^2$/sec/Pa)

(2) Evaluation of Promoter Activity

The viable cell count (cell/mL) of the bacterial cells collected in the section (1) was measured by "CountStar" (manufactured by Aber Instruments Ltd.; measurement method: standard). Further, the bacterial cells were diluted as appropriate, and the fluorescence intensity was measured under the conditions of Ex: 530 nm and Em: 590 nm, by a multi-plate reader ("Synergy HT-I" (manufactured by BioTek Instruments, Inc.)). The thus obtained fluorescence intensity was divided by the viable cell count to calculate the fluorescence intensity (count/cell/mL) per viable cell count, and the promoter activity was measured. The results are summarized in Table 3.

Comparative Example 1 Preparation of CMV Promoter Recombinant Yeast (1) Obtaining Plasmid Vector The mRuby gene was extracted from the plasmid prepared in Example 1, using restriction enzymes Sac1 (available from New England Biolabs, Inc.) and Sal1 (available from New England Biolabs, Inc.), and introduced into the Sac1 and Sal1 sites of pAUR224 (available from Takara Bio Inc.), using "Ligation-Convenience Kit" (manufactured by Nippon Gene Co., Ltd.), to obtain pAUR224-mRuby.

(2) Obtaining Transformant

The pAUR224-mRuby obtained in the section (1) was introduced into *Schizosaccharomyces pombe* 972h- to perform transformation, in the same manner as in the section (2) in Example 2, to obtain a recombinant yeast pAUR224-mRuby strain.

Comparative Example 2 Evaluation of CMV Promoter Activity

Cultured bacterial cells were obtained and the evaluation of the promoter activity was performed for the recombinant yeast pAUR224-mRuby strain obtained in Comparative Example 1, in the same manner as in the sections (1) and (2) in Example 3. The results are summarized in Table 3.

TABLE 3

| | Promoter Activity (count/cell/mL) | |
|---|---|---|
| Culture Phase | CMV (Comparative Example 2) | TCTP1 (Example 3) |
| Batch Phase | $8.2 \times 10^{-6}$ | $1.6 \times 10^{-5}$ |
| Continuous Culture Phase | $4.0 \times 10^{-5}$ | $7.2 \times 10^{-5}$ |

Example 4 Preparation of Recombinant Yeast (1) Obtaining Plasmid Vector pAURTCTP1-mScarlet or pAURTCTP2-mScarlet in which the TCTP1 promoter, or the TCTP promoter (hereinafter, also referred to as "TCTP2) of SEQ ID NO: 5, had been inserted between the Nco1 and Xho1 recognition sites of pAUR224 (available from Takara Bio Inc.), and in which the gene of a fluorescent protein, mScarlet (FPbase ID: FVS3D), had been linked to the downstream thereof, was obtained by the GENEWIZ gene synthesis service.

(2) Obtaining Transformant

The pAURTCTP1-mScarlet or the pAURTCTP2-mScarlet obtained in the section (1) was introduced into *Schizosaccharomyces pombe* 972h-, in the same manner as in the section (2) in Example 2, to obtain a recombinant yeast pAURTCTP1-mScarlet strain or pAURTCTP2-mScarlet strain.

Example 5 Evaluation of Promoter Activity (1) Continuous Culture of Recombinant Yeast The continuous culture using a separation membrane was carried out in the same manner as in the section (1) in Example 3, using the recombinant yeast pAURTCTP1-mScarlet strain or pAURTCTP2-mScarlet strain, to collect bacterial cells for measuring the activity, for each kind.

(2) Evaluation of Promoter Activity

The viable cell count (cell/mL) of each kind of the bacterial cells collected in the section (1) was measured by "CountStar" (manufactured by Aber Instruments Ltd.; measurement method: standard). Further, each kind of the bacterial cells were diluted as appropriate, and the fluorescence intensity was measured under the conditions of Ex: 540 nm and Em: 620 nm, by a multi-plate reader ("Synergy HTX" (manufactured by BioTek Instruments, Inc.)). The thus obtained fluorescence intensity was divided by the viable cell count to calculate the fluorescence intensity (count/cell/mL) per viable cell count, and the promoter activity was measured, for each kind. The results are summarized in Table 4.

Comparative Example 3 Preparation of CMV Promoter Recombinant Yeast (1) Obtaining Plasmid Vector Primers were designed so that the mScarlet gene can be introduced into the Xho1 site of pAUR224 (available from Takara Bio Inc.) using "In Fusion" (manufactured by Takara Bio Inc.), in accordance with the method described in the manual of the kit. Then the mScarlet gene was amplified by PCR, using the plasmid prepared in the section (1) in Example 4 as a template. Thereafter, the amplified gene was introduced into the Xho1 site of pAUR224 (available from Takara Bio Inc.) using "In Fusion" (manufactured by Takara Bio Inc.), to obtain pAUR224-mScarlet.

(2) Obtaining Transformant

The pAUR224-mScarlet obtained in the section (1) was introduced into *Schizosaccharomyces pombe* 972h-, in the same manner as in the section (2) in Example 2, to obtain a recombinant yeast pAUR224-mScarlet strain.

Comparative Example 4 Evaluation of CMV Promoter Activity

Cultured bacterial cells were obtained and the evaluation of the promoter activity was performed for the recombinant yeast pAUR224-mScarlet strain obtained in Comparative Example 1, in the same manner as in the sections (1) and (2) in Example 5. The results are summarized in Table 4.

TABLE 4

| | Promoter Activity (count/cell/mL) | | |
|---|---|---|---|
| Culture Phase | CMV (Comparative Example 4) | TCTP1 (Example 5) | TCTP2 (Example 5) |
| Batch Phase | $1.0 \times 10^{-5}$ | $3.2 \times 10^{-5}$ | $2.7 \times 10^{-5}$ |
| Continuous Culture Phase | $5.2 \times 10^{-5}$ | $8.4 \times 10^{-5}$ | $8.5 \times 10^{-5}$ |

It has been confirmed from the results of Examples 1, 3 and 5 that the TCTP promoter is a promoter which is highly expressed in a *Schizosaccharomyces* yeast, during the continuous culture thereof. Further, it has been confirmed from the results of Example 5 and Comparative Example 4 that the function as the promoter can be achieved as long as the promoter contains the nucleotide sequence of SEQ ID NO: 5, and that the TCTP promoter is expressed at a higher level as compared to the CMV promoter. Based on the above, it has been evaluated that the use of a nucleic acid construct in which a polynucleotide of interest is linked to the downstream of the TCTP promoter allows the polynucleotide of interest to be highly expressed during the continuous culture.

The invention claimed is:

1. A nucleic acid construct, comprising a translationally controlled tumor protein (TCTP) gene promoter derived from a *Schizosaccharomyces* yeast, and a polynucleotide fragment, wherein said polynucleotide fragment is artificially linked downstream of said promoter to be expressed under the control of said promoter.

2. The nucleic acid construct according to claim 1, wherein said *Schizosaccharomyces* yeast is *Schizosaccharomyces pombe, Schizosaccharomyces octosporus, Schizosaccharomyces cryophilus* or *Schizosaccharomyces japonicus.*

3. The nucleic acid construct according to claim 1, wherein said promoter comprises the 5'-untranslated region of said TCTP gene, and said polynucleotide fragment is artificially linked downstream of said untranslated region.

4. The nucleic acid construct according to claim 1, wherein said promoter is a polynucleotide comprising the nucleotide sequence of (a) or (b):

(a) a polynucleotide composed of the nucleotide sequence of any one of SEQ ID NOs: 1 to 4;

(b) a polynucleotide composed of a nucleotide sequence having a sequence identity of 85% or more to the nucleotide sequence of any one of SEQ ID NOs: 1 to 4.

5. The nucleic acid construct according to claim 1, wherein said promoter is a polynucleotide comprising the nucleotide sequence of (c) or (d):

(c) a polynucleotide composed of the nucleotide sequence of any one of SEQ ID NOs: 5 to 8;

(d) a polynucleotide composed of a nucleotide sequence having a sequence identity of 85% or more to the nucleotide sequence of any one of SEQ ID NOs: 5 to 8.

6. The nucleic acid construct according to claim 1, wherein said polynucleotide fragment encodes a protein.

7. A recombinant *Schizosaccharomyces* yeast, comprising the nucleic acid construct according to claim 1.

8. A method of expressing a polynucleotide, the method comprising a step of continuously culturing the recombinant *Schizosaccharomyces* yeast according to claim 7.

9. The method of expressing a polynucleotide according to claim 8, wherein said continuous culture comprises the step of filtering a culture liquid obtained by culturing said yeast through a separation membrane, retaining or returning the unfiltered liquid containing said yeast in or to said culture liquid, and adding a fermentation feedstock to said culture liquid.

10. A method of producing a chemical product, the method comprising the step of culturing the recombinant *Schizosaccharomyces* yeast according to claim 7.

11. The method of producing a chemical product according to claim 10, wherein said culture is continuous culture.

12. The method of producing a chemical product according to claim 11, wherein said continuous culture comprises the step of filtering a culture liquid obtained by culturing said yeast through a separation membrane, retaining or returning the unfiltered liquid containing said yeast in or to said culture liquid, and adding a fermentation feedstock to said culture liquid.

* * * * *

SEQUENCE LISTING

```
Sequence total quantity: 8
SEQ ID NO: 1            moltype = DNA  length = 400
FEATURE                 Location/Qualifiers
source                  1..400
                        mol_type = unassigned DNA
                        organism = unidentified
                        note = Schizosaccharomyces pombe
SEQUENCE: 1
atggttcaat tgttgaattc atttggactt taattccagc tttaatctta attttacacg  60
catcataatg gtttcactca aaaaatcaga ttcagtaata taaaacaatt tactactgac  120
tgagtacaac gatattttca tctaaaaaaa aatctgaaaa tataaagaat attgttattt  180
aaaagaaagg agaacagact acgacaaatt gaaaaaaatg aaggaattgg taaacaaaat  240
gtatctatcg aaaacaacgc tgtactacgt aaagtgaata ctgttcgtaa ccgcattcca  300
tacggatggc tagaatccag taaccctgcc ctaaactgtg actgctttat ctcattaaac  360
ctgcgagaag tcaaattatg agctaccatc tgcaatcacc                        400

SEQ ID NO: 2            moltype = DNA  length = 216
FEATURE                 Location/Qualifiers
source                  1..216
                        mol_type = unassigned DNA
                        organism = unidentified
                        note = Schizosaccharomyces octosporus yFS286
SEQUENCE: 2
gctcatatat attctttttc ttttacatca aatataaaat acgccttata aactatagct  60
aatatcatcc gtgtttaatg agtatcacta tatttcatac tacgatgata acccaattaa  120
cccattcata gaaaccctta ccctggtgtg actggtattc aggaagtcgg catgagaaaa  180
accggatgca ttaacttgtc ttccacattc accacc                            216

SEQ ID NO: 3            moltype = DNA  length = 341
FEATURE                 Location/Qualifiers
source                  1..341
                        mol_type = unassigned DNA
                        organism = unidentified
                        note = Schizosaccharomyces cryophilus OY26
SEQUENCE: 3
aaagacattc tttctcaatc ctggtatcac tcgaatttcc gatttcattg aagaataata  60
cttggtgaaa ctgggttaat tatacatcta ttatttactt tacaaattac gtcctacctc  120
caataaacag ttcctcatcc ttcctcacag atgcaaaaac ttatgctact ctcattctgt  180
gcctgtttat cacatttagc tttccatact aaataaccat gaacttgcat attcgatata  240
ttttctcttg tgaccagaaa ccctaaccta ctgtgaccgg ttttccctca acgaggaagg  300
aagagactgg ctgtaacaat ttttcatcca caatcaccac c                      341

SEQ ID NO: 4            moltype = DNA  length = 375
FEATURE                 Location/Qualifiers
source                  1..375
                        mol_type = unassigned DNA
                        organism = unidentified
                        note = Schizosaccharomyces japonicus FS275
SEQUENCE: 4
tatagttgtg atcacttgga agtttgttat tgatttttac tttcgtatta ttgatattga  60
ttttaattca tttgtttatt ctgaattatg ttactgctgc tactgcaatt gttgttgttg  120
ttgttattgt cactattatc tatttgtttt taccaattac aattacaatt ttattttttt  180
tattttaatt tatctttact ttactttgct tcacttcact tacttattat tctcccccac  240
ctctccctaa ccccgccaca cccctcgttg cacctcgcta caccccatta cgctaccccc  300
acaccccgct gtgactgcta ccacgacaca cccaaatcac gcttctcgcg ctgccaccct  360
ctaccaacca ccacc                                                   375

SEQ ID NO: 5            moltype = DNA  length = 105
FEATURE                 Location/Qualifiers
source                  1..105
                        mol_type = unassigned DNA
                        organism = unidentified
                        note = Schizosaccharomyces pombe
SEQUENCE: 5
ttccatacgg atggctagaa tccagtaacc ctgccctaaa ctgtgactgc tttatctcat  60
taaacctgcg agaagtcaaa ttatgagcta ccatctgcaa tcacc                  105

SEQ ID NO: 6            moltype = DNA  length = 116
FEATURE                 Location/Qualifiers
source                  1..116
                        mol_type = unassigned DNA
                        organism = unidentified
                        note = Schizosaccharomyces octosporus yFS286
SEQUENCE: 6
tacgatgata acccaattaa cccattcata gaaaccctta ccctggtgtg actggtattc  60
aggaagtcgg catgagaaaa accggatgca ttaacttgtc ttccacattc accacc      116

SEQ ID NO: 7            moltype = DNA  length = 116
```

-continued

```
FEATURE                 Location/Qualifiers
source                  1..116
                        mol_type = unassigned DNA
                        organism = unidentified
                        note = Schizosaccharomyces cryophilus OY26
SEQUENCE: 7
tgcatattcg atatattttc tcttgtgacc agaaacccta acctactgtg accggttttc  60
cctcaacgag gaaggaagag actggctgta acaatttttc atccacaatc accacc      116

SEQ ID NO: 8            moltype = DNA  length = 203
FEATURE                 Location/Qualifiers
source                  1..203
                        mol_type = unassigned DNA
                        organism = unidentified
                        note = Schizosaccharomyces japonicus FS275
SEQUENCE: 8
atttttttta ttttaattta tctttacttt actttgcttc acttcactta cttattattc  60
tcccccacct ctccctaacc ccgccacacc cctcgttgca cctcgctaca ccccattacg  120
ctacccccac accccgctgt gactgctacc acgacacacc caaatcacgc ttctcgcgct  180
gccaccctct accaaccacc acc                                          203
```